United States Patent
Oksala et al.

(10) Patent No.: US 10,827,934 B2
(45) Date of Patent: Nov. 10, 2020

(54) METHOD, DEVICE AND ARRANGEMENT FOR DETERMINING PULSE TRANSIT TIME

(71) Applicant: Nokia Technologies Oy, Espoo (FI)

(72) Inventors: Niku Oksala, Tampere (FI); Antti Vehkaoja, Tampere (FI); Sami Melkoniemi, Espoo (FI)

(73) Assignee: Nokia Technologies Oy, Espoo (FI)

( * ) Notice: Subject to any disclaimer, the term of this patent is extended or adjusted under 35 U.S.C. 154(b) by 654 days.

(21) Appl. No.: 15/318,995

(22) PCT Filed: Jun. 17, 2015

(86) PCT No.: PCT/FI2015/050443
§ 371 (c)(1),
(2) Date: Dec. 15, 2016

(87) PCT Pub. No.: WO2015/193551
PCT Pub. Date: Dec. 23, 2015

(65) Prior Publication Data
US 2017/0143216 A1  May 25, 2017

(30) Foreign Application Priority Data
Jun. 18, 2014 (FI) ..................... 20145587

(51) Int. Cl.
*A61B 5/021* (2006.01)
*A61B 5/00* (2006.01)
*A61B 5/024* (2006.01)

(52) U.S. Cl.
CPC ........ *A61B 5/02125* (2013.01); *A61B 5/0022* (2013.01); *A61B 5/02422* (2013.01);
(Continued)

(58) Field of Classification Search
CPC .............. A61B 5/02125; A61B 5/0022; A61B 5/02422; A61B 5/6824; A61B 5/681;
(Continued)

(56) References Cited

U.S. PATENT DOCUMENTS 8,604,923 B1 * 12/2013 Rivas Alvarez ... A61B 5/02055
340/539.12
8,827,906 B2 * 9/2014 Yuen .................... A61B 5/6885
600/301
(Continued)

FOREIGN PATENT DOCUMENTS

JP  2004305268 A  * 11/2004
KR  101337387  12/2013
(Continued)

OTHER PUBLICATIONS

Extended European Search Report for European Patent Application No. 15809850.9 dated Dec. 14, 2017, 8 pages.
(Continued)

*Primary Examiner* — Jacqueline Cheng
*Assistant Examiner* — Tho Q Tran
(74) *Attorney, Agent, or Firm* — Locke Lord LLP

(57) ABSTRACT

An arrangement (100) and a device (101) for determining pulse transit time comprise an accelerometer (102) and a pulse wave sensor (103) for sensing a pulse wave. The accelerometer (102) determines a cardiac systole, and the pulse wave sensor (103) determines the pulse wave induced by said cardiac systole ejection. A first trigger signal is determined at the moment of said determined cardiac systole, and a second trigger signal at the moment of said determined pulse wave. The pulse transit time is then determined as a time difference between said first and second trigger signals.

14 Claims, 1 Drawing Sheet

(52) U.S. Cl.
CPC .......... *A61B 5/6824* (2013.01); *A61B 5/0002* (2013.01); *A61B 5/02133* (2013.01); *A61B 5/681* (2013.01); *A61B 2560/0223* (2013.01); *A61B 2562/0219* (2013.01)

(58) Field of Classification Search
CPC ........ A61B 2560/0223; A61B 5/02133; A61B 2562/0219; A61B 5/0002
USPC ......................................................... 600/500
See application file for complete search history.

(56) References Cited

U.S. PATENT DOCUMENTS

| | | | |
|---|---|---|---|
| 2004/0039420 A1 | 2/2004 | Jayne et al. | |
| 2006/0264771 A1* | 11/2006 | Lin ...................... | A61B 5/0205 600/513 |
| 2008/0066753 A1* | 3/2008 | Martin .............. | A61M 16/0051 128/204.23 |
| 2008/0183232 A1* | 7/2008 | Voss .................. | A61B 5/02028 607/24 |
| 2010/0160798 A1 | 6/2010 | Banet et al. | |
| 2010/0298650 A1 | 11/2010 | Moon et al. | |
| 2011/0009754 A1* | 1/2011 | Wenzel ................ | A61B 5/0215 600/485 |
| 2011/0112442 A1 | 5/2011 | Meger et al. | |
| 2013/0296723 A1 | 11/2013 | Cho et al. | |
| 2015/0080746 A1* | 3/2015 | Bleich ................ | A63B 69/0028 600/479 |
| 2017/0281024 A1* | 10/2017 | Narasimhan ....... | A61B 5/02125 |
| 2018/0042494 A1* | 2/2018 | Barodka .............. | A61B 5/6829 |

FOREIGN PATENT DOCUMENTS

| | | |
|---|---|---|
| WO | WO2011039580 | 4/2011 |
| WO | WO2014022906 | 2/2014 |
| WO | WO2015061579 | 4/2015 |

OTHER PUBLICATIONS

International Search Report for International Patent Application No. PCT/FI2015/050443, dated Oct. 16, 2015, 7 pages.
PCT Written Opinion of the International Searching Authority for International Patent Application No. PCT/FI2015/050443, dated Oct. 16, 2015, 8 pages.
English Language Machine Translation of Abstract for Korean Patent Publication No. KR101337387, Published: Dec. 16, 2013, 2 pages.
Winokur, E. S. et al., "A Wearable Vital Signs Monitor at the Ear for Continuous Heart Rate and Pulse Transit Time Measurements", Conf. Proc. IEEE Eng. Med. Biol. Soc., 2012, 14 pages.
European Examination Report for European Patent Application No. 15809850.9 dated Oct. 12, 2018, 5 pages.

\* cited by examiner

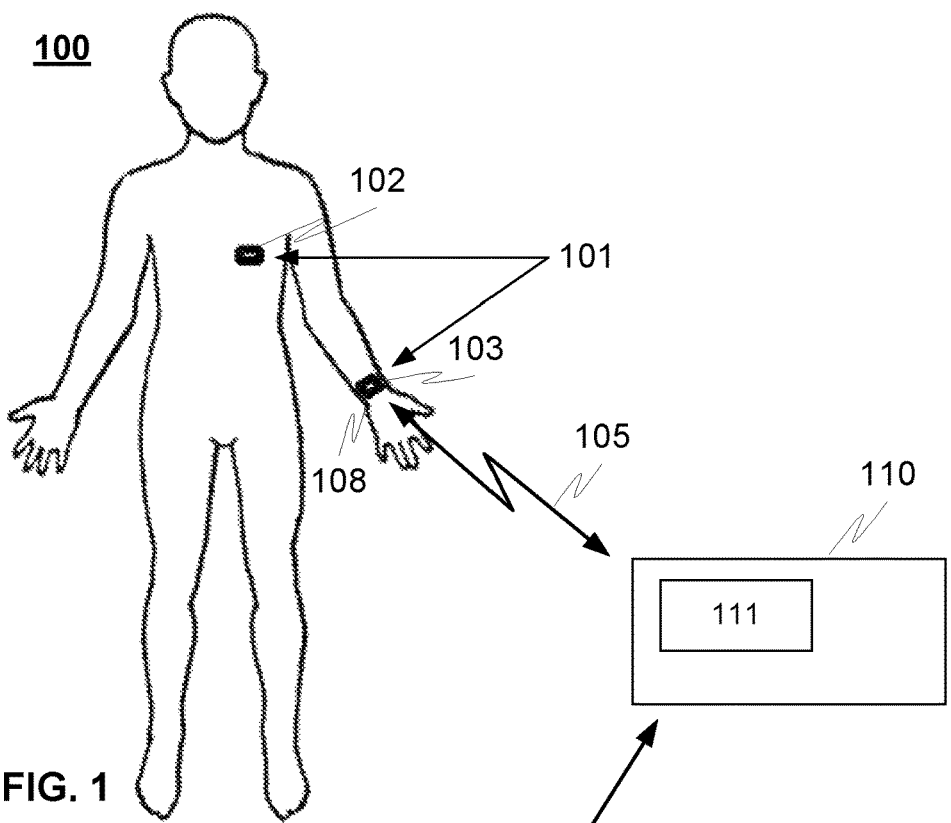
FIG. 1
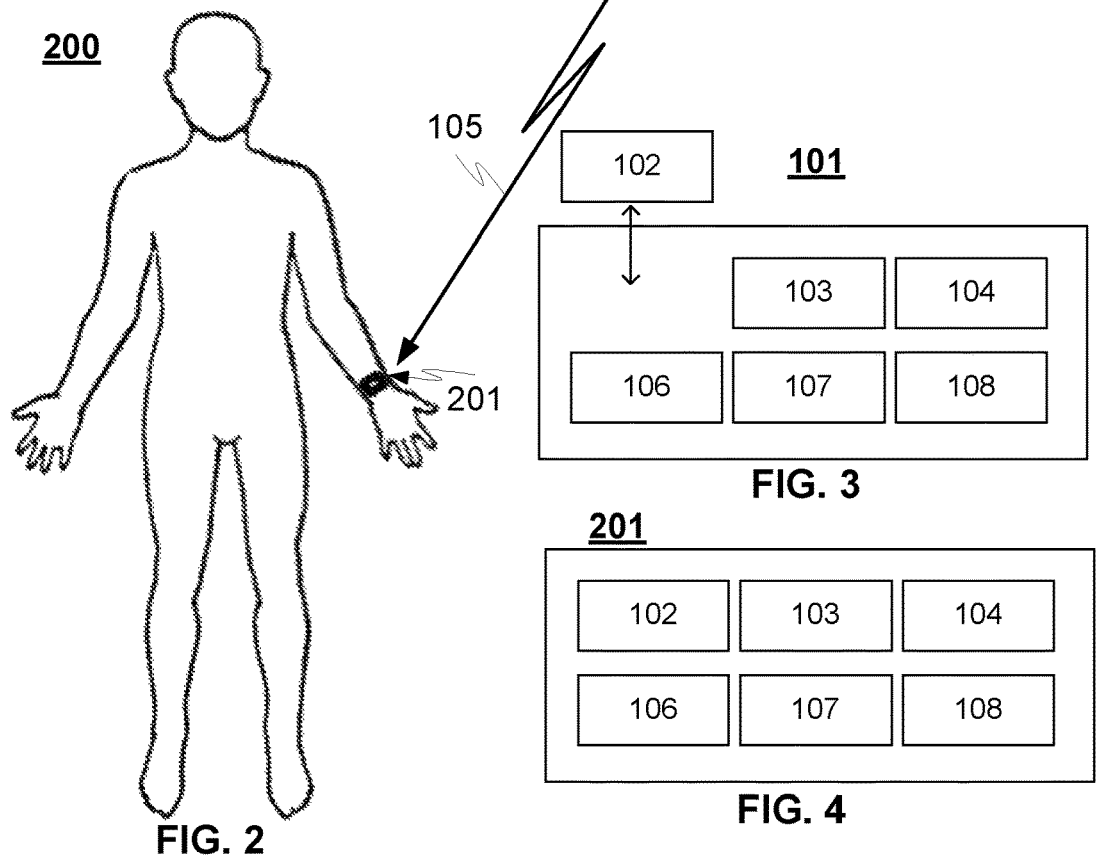
FIG. 2
FIG. 3
FIG. 4

METHOD, DEVICE AND ARRANGEMENT FOR DETERMINING PULSE TRANSIT TIME

TECHNICAL FIELD OF THE INVENTION

The invention relates to a method, device and arrangement for determining pulse transit time especially of a pulse propagating through a blood vessel. In addition the invention relates to a method, device and arrangement for determining pulse wave velocity and thereby arterial blood pressure based on said pulse transit time.

BACKGROUND OF THE INVENTION

Blood pressure is an important vital parameter. It is conventionally measured by devices relying on intermittent tourniquet based technology. The intermittent measurement has several disadvantages, namely it is slow and cumbersome, causes significant discomfort, includes mechanical moving parts prone to wear and technical errors. In addition it blocks the blood circulation making other measurements invalid. Some continuous measurement systems exist based on a determination of PTT (Pulse Transit Time), where the pulse propagating in the blood vessel is detected at two distinct points at a known distance apart and based on the wave velocity the blood pressure can be determined after external calibration, e.g. baseline calibration. However, the results of these continuous measurement systems are not typically reliable due to changing environmental artefacts, motion of the user and motion or positioning of the measuring device in the best position for ensuring reliable signals.

The continuously measuring prior art solutions rely on measurement of PTT using analysis of pulse wave (PW) by different combinations of sensors attached in the chest (i.e. ECG, impedance cardiography, acoustoelectric transducer) and peripheral PW sensors (e.g. photo pulse plethysmography PPG, or pressure sensors) attached on either the fingertip or finger base. In previous art, PTT measurement utilizing ECG R-peak and peripheral pressure transducer pulse wave at the wrist above the radial artery or on any artery at the wrist has been demonstrated. Previously also infrared sensors are utilized for the compensation of individual conditions according to a user, such as position and the depth of an artery. A system based on ECG and a pressure cuff has also been demonstrated. Also a system is known which utilized ECG and optoelectric sensors in ear lobes. PTT can also be measured locally utilizing two piezoelectric detectors or utilizing two peripheral PPG sensors at wrist and finger base thus avoiding the need for simultaneous ECG recording. These solutions are problematic since the finger vasculature is subject to constant vasoregulatory oscillation which alters the caliber of the artery thus resulting in significant alterations in the pulse wave propagation. This solution is also subject to significant motion artifact. PTT measurement based on time difference between the ECG R-peak and the peripheral pulse wave is susceptible to error due to alteration of cardiac pre-ejection period (PEP) especially in the critically ill patients since it is related with fluid shifts within the body induced by posture changes and also due to factors not necessarily related to systemic blood pressure alone.

SUMMARY OF THE INVENTION

An object of the invention is to alleviate and eliminate the problems relating to the known prior art. Especially the object of the invention is to provide an arrangement and device, which is pleasant and fast to use, measures continuously and does not block blood circulation. In addition the object is to provide a device, which is not so vulnerable to motion of the user or motion or positioning of the measuring device, or to vasoregulatory oscillation and alteration of cardiac pre-ejection period (PEP).

The object of the invention can be achieved by the features of independent claims.

The invention relates to a device according to claim 1. In addition the invention relates to a method according to claim 15 and to a computer program product according to claim 16. The invention further relates to an arrangement according to claim 21.

According to an embodiment of the invention a pulse transit time (PTT) is determined by an accelerometer and a pulse wave sensor so that the cardiac systole is determined by the accelerometer and the pulse wave induced by the cardiac systole ejection is determined by the pulse wave sensor. The cardiac systole ejection, i.e. the mechanic contraction of the cardiac muscle resulting in opening of the aortic valve, induces a wave, such as a seismic wave, which is transmitted at a certain speed thought the body, like bones and muscles. This wave induced by the cardiac systole results again an acceleration signal, which can be determined by the accelerometer. According to an example a speed of sound can be used in the calculations and determinations.

According to the invention a first trigger signal is determined at the moment of said determined cardiac systole, and a second trigger signal at the moment of said determined pulse wave. The pulse transit time can thus be determined as a time difference between said first and second trigger signals. When the distance between the heart and the measuring point of the pulse wave is known, the pulse wave velocity can be determined and thereby also arterial blood pressure. For this a baseline calibration may be needed. The distance between the heart and the measuring point of the pulse wave can be measured by a tape or the like, for example, or by the accelerometer(s) and pulse wave sensor (s), as described elsewhere in this document.

The pulse wave sensor may be any sensor suitable for measuring pulse wave at the measuring point, such as an optical sensor (PPG) for sensing changes in the amount of blood in the arteries at the measuring point due to pulse wave, or a pressure measuring device, a capacitive sensor, passive infrared sensor, CMOS cell, or EMFI film or piezoelectric sensor determining corresponding changes induced by the pulse wave at the measuring point. According to an advantageous embodiment, the pulse wave sensor may be implemented by an accelerometer, which detects accelerations due to pulse waves at the measuring point.

It is to be noted that according to an embodiment an accelerometer is used for determining said cardiac systole ejection, i.e. the mechanic contraction of the cardiac muscle resulting in opening of the aortic valve. The accelerometer may be a separate accelerometer that locates at the point of the heart, but according to an embodiment of the invention the accelerometer may be the same as used for determining the pulse wave. The seismic wave induced by the cardiac systole ejection is transmitted at a certain speed thought the body, like bones and muscles, and can thus be determined by the accelerometer also at the measuring point of pulse wave. The acceleration signal due to the pulse wave has a different form than the acceleration signal induced by the cardiac systole ejection, whereupon the same accelerometer can be used both for determining the cardiac systole ejection as well as the resulting pulse wave. Thus, according to an embodiment, the device for determining the PPT (with accelerometer, for example) can be implemented by a wristband like device.

According to an embodiment the distance between the heart and the measuring point of the pulse wave is determined based on the time difference between the first and second trigger signals by using the certain known speed as a speed of acceleration signal transferred from the heart to the accelerometer. According to an embodiment also a vibration device can be used for determining the distance, wherein the vibration device is positioned at the measuring position, and a separate accelerometer is used at the point of heart. In this embodiment vibration signal is generated by the vibration device, said vibration signal being transmitted though the body, like bones and muscles, at the certain speed (a speed of sound) similarly than the seismic wave induced by the cardiac systole ejection described elsewhere in this document. This vibration signal induces acceleration signal (s) at the body, which can be detected by the accelerometer or another type of sensor. When the accelerometer is located at the point of the heart, the distance can be determined when the time taken to the propagation of the vibration signal from the vibration device to the accelerometer is known (determined) and when the assumption of the velocity of the vibration signal (speed of sound) is used.

According to an example the vibration device is turned on, and as the sound propagates at a constant speed, the delay from the vibrator at the measuring point to the accelerometer at the chest or heart area can be measured, therefore the distance can be calculated using the constant velocity. Still according to an example, the sampling rate of the sensors may be at a magnitude of at 250 Hz, more advantageously at least 1 kHz. It is to be understood that the data processing may be performed either by the device worn by the user or in a separate backend system (application, computer, smartphone, server, cloud based system or the like), whereupon the device comprises advantageously wireless data communication means for communicating the measurement signals to the backend. The device may be configured to detect movements of the body and upper extremity based on the measurement data of said accelerometers (ACC1, 2, 3). It is to be noted that the device additionally comprises also other components allowing the measurements, such as an MCU or ASIC logic circuit, power source, like a battery, analog-to-digital conversion units, synchronized radio transceivers.

The accelerometer may be implemented by the devices suitable for measuring accelerations described in this document, such as by a 1D, 2D, or 3D MEMS accelerometer or gyroscope or magnetometer.

Next one example of the invention is described in more details, but it is to be noted that this should not be interpreted as limiting the scope of the claims, but this is only as an example. According to an example a separate accelerometer used at the chest area (chest band device, CB) comprises at least one but advantageously two 3D MEMS accelerometers advantageously but not mandatorily supplemented with gyroscopes and magnetometers, the first of which is advantageously located left and lateral to the left edge of sternum (ACC1), for example above the 3rd-5th intercostal spaces, advantageously above the apex of the heart but not necessarily limited to these locations along the thoracic area. Other preferable locations are those areas with little subcutaneous fat and bony structures beneath such as sternal area and along the costal arch. The second 3D MEMS accelerometer is located advantageously right and lateral to the right edge of the sternum (ACC2), symmetrically to the first 3D MEMS sensor, within thoracic area but not necessarily limited to that location. For the detection of the heartbeat, the first accelerometer (ACC1) can also be located along the course of clavicle, scapula, preferably but not limited to epicondyles of the humerus and preferably but not limited to processes styloideus radii and ulnae due to the efficient conduction of heart pulse along these bone structures.

It is to be noted that the design above ultimately allows also the construction of a device or arrangement comprising all the sensors in a single device located at the wrist and therefore without separate CB device based on assumption that the seismic pulse induced by heart systole is transmitted at a speed of sound and therefore there is negligible delay between the pulse at the wrist area and at the heart. This design allows for the ACC1 sensor to be positioned so that it can measure the mechanical movement caused by the heartbeat at maximum signal to noise ratio at least in a subject lying supine and still.

According to an example the peripheral wristband device (WB) comprises a distal sensor which can be a pulse photo plethysmograph (PPG), a capacitive sensor, a passive infrared sensor, a CMOS cell, an accelerometer or EMFI film based sensor (DIST). The WB sensor (such as a PPG sensor) is capable of measuring the pulse wave for the determination of a fiducial point in it and possibly the heart rate from the CB and/or WB sensors. WB may also comprise a similar 3D-MEMS accelerometer (ACC3) as the CB. PTT may then be calculated by identification of characteristic points in the heart beat acceleration waveform and a fiducial point defined in the DIST sensor's waveform and determination of the duration of the pulse wave propagation between these points, i.e. PTT. Either first derivative, second derivative, minimum-maximum-intersecting tangents, foot point, adaptive threshold or another method can be used to identify the fiducial points. The measurement may be calibrated at the beginning of measurement using either external blood pressure measurement system or by utilizing different positions of the arm resulting in changing hydrostatic pressure which can be calculated using the radius of the upper extremity. An example of the calibration procedure is described elsewhere in this document.

According to an embodiment the accelerometers (ACC1, 2, 3) can also be used for baseline calibration. Blood pressure measurement should advantageously be performed so that the measurement point stays at a constant distance from the heart. The accelerometer sensors can yield the change in vertical displacement of WB relative to CB using basic trigonometry while upper extremity is retained straight throughout the maneuver. Therefore, the system can automatically calibrate to different measurement conditions. To convert relative measures to absolute ones, a user specific calibration procedure may be performed so that when lying supine, the upper extremity is raised or flexed straight at an angle of 90° relative to the horizontal plane. This procedure can be monitored, according to an exemplary embodiment, by the accelerometers (ACC1, 2, 3) and the PWV calculation algorithm is executed when the 90° angle relative to earth gravity vector is achieved.

Using the equation (1), where $\Delta h$ is the altitude change during the baseline calibration (measured manually or by utilization of a specific horizontal calibration maneuver in which the distance between two accelerometers located to the arm is known and the radius of the horizontal movement is calculated by utilization of the difference in the centripetal acceleration between the accelerometers), $\rho$ is the density of blood and g is the gravitational constant the absolute change in hydrostatic pressure is calculated:

$$\Delta P_{hydrostatic} = \Delta h \rho g \quad (1)$$

Using this equation, the association of the PTT values can be calibrated to absolute values. Alterations in the PWV and the PTT have been shown to correlate well with alterations in systemic arterial pressure. However, interpersonal correlation is weaker. The signal processing algorithm may be integrated in the signal processing unit of the component itself or located in a remote backend system. The PWV can be calculated from the PTT when the effective distance between the CB and WB is measured. The absolute pressure values are derived by first utilizing the Moens-Korteweg equation (2), where t is the thickness of the artery wall, d is the diameter of the artery, ρ is the density of blood which is considered constant, and E is the Young's modulus reflecting the elasticity of the arterial wall:

$$PWV = \sqrt{\frac{tE}{\rho d}} \quad (2)$$

The Young's modulus E is not constant but varies with arterial pressure. The dependence of E on the pressure is shown by equation (3), where $E_0$ is the zero pressure modulus, α is a vessel constant, P is the arterial pressure and e is the Euler number:

$$E = E_0 e^{\alpha P} \quad (3)$$

When the equation (3) is substituted to the equation (2) it yields equation (4) which describes the association of PWV with P and zero pressure elasticity $E_0$:

$$PWV = \sqrt{\frac{tE_0 e^{\alpha P}}{\rho d}} \quad (4)$$

From this equation P can be solved and the values of unknown coefficients (t, α, d) are determined during the individual baseline calibration procedure utilizing pressure change (equation 1). This association can also be utilized for continuous correction of the measurement by changes in upper extremity position using accelerometer data (ACC1, 2, 3) for the calculation of the hydrostatic pressure change.

The present invention offers advantages over the know prior art, such as the possibility to eliminate errors due to PEP by utilizing techniques other than ECG for the timing of the mechanical contraction of the heart, i.e. systole. In addition the present invention offers continuous measurements of the arterial signals, such as PTT and thereby the blood pressure with improved accuracy. The method requires no simultaneous ECG recording and therefore there is no need for multiple sensors attached to the chest. In addition when using a device, e.g. accelerometer or the like, for determining the acceleration signals due to the cardiac systole ejection, there is necessarily no need for any sensor at the chest area, which is clear advantage. Moreover also environmental factors may be taken into account and thereby ensuring reliable signals by selective discrimination of signals during heavy movement. Especially it is to be noted that measurements can be done without any direct blood pressure measurements, such as tourniquet techniques or sensors which should be pressed tightly against the body, which offers clear advantages. Furthermore the distance between the heart and the pulse wave measuring point can be easily and accurately detected by the device even without any separate measurement, such as using any clumsy tape or meters.

BRIEF DESCRIPTION OF THE DRAWINGS

Next the invention will be described in greater detail with reference to exemplary embodiments in accordance with the accompanying drawings, in which:

FIGS. 1-2 illustrates principles of exemplary arrangements for determining pulse transit time according to an advantageous embodiment of the invention, and FIGS. 3-4 illustrate principles of exemplary devices for determining pulse transit time according to an advantageous embodiment of the invention.

DETAILED DESCRIPTION

FIGS. 1-2 illustrates principles of exemplary arrangements 100, 200 for determining pulse transit time and FIGS. 3 and 4 principles of exemplary devices 101, 201 for determining pulse transit time according to an advantageous embodiment of the invention.

FIG. 1 illustrates an exemplary arrangement 100 according to an advantageous embodiment of the invention, wherein the arrangement comprises advantageously a device 101 having sensors 102, 103 for performing measurement of signals, and additionally also a backend system 110 for calculating results, such as PTT, PWV or blood pressure. The device comprises advantageously also a data communication device 104 for communicating 105 the measured data signals to the backend 110. The device may also comprise a data communication device 104 for receiving determined or calculated data from the backend for example for displaying purposes, whereupon the device comprises also a display 106. Anyway it should be noted that the device may also comprise the data processing devices 107 for determining the results, whereupon there is no need for any backend system 110. The backend system may be for example an application run on a computer, smartphone, server, cloud based system or the like.

The arrangements 100, 200 for measuring pulse transit time comprises an accelerometer 102 and a pulse wave sensor 103 for sensing a pulse wave induced by a heartbeat and transmitted via a blood vessel. The accelerometer 102 is configured to determine a cardiac systole i.e. the mechanic contraction of the cardiac muscle resulting in opening of the aortic valve. The pulse wave sensor 103 is configured to determine the pulse wave induced by said cardiac systole ejection. Said accelerometer 102 and a pulse wave sensor 103 are advantageously comprised by the device 101 either as a separate module, or as integrated into the same device 201. The device 101, 201 may comprise also the data processing device 107 to determine a first trigger signal at the moment of said determined cardiac systole (when receiving signal from the device determining said cardiac systole, such as the accelerometer 102), and a second trigger signal at the moment of said determined pulse wave.

As an example the device 101 communicates 105 said measured signals or derivatives of them, such as the first and second trigger signals to the backend system 110, which comprises a data processing device 111 for determining the pulse transit time as a time difference between said first and second trigger signals.

The arrangement, such as the device 101, 201 or data processing device 111 of the backend system is configured to determine said pulse wave velocity based on the time difference, when distance between the heart and the pulse wave sensor 103 is determined, and thereby also the arterial blood pressure. It is to be noted that a baseline calibration may also be needed, which can be performed by the device, arrangement and/or the data processing device or their combination by the steps describes elsewhere in this document.

As an example the arrangement 200 may comprise an accelerometer 102 positioned at the measurement point of the pulse wave 103, such as at the wristband device 201. The accelerometer 102 or the wristband device 201 is advantageously configured to determine a cardiac systole via said accelerometer 102 based on an acceleration signal incurred by the heart at the moment of the cardiac systole, as described in this document. In addition wristband device 201 together with the said accelerometer 102 or by other pulse wave detecting device 103 is configured to determine the pulse wave at the measuring point 103. When the accelerometer 102 is used as the pulse wave detecting device (instead of other pulse wave detecting device, as described in FIG. 2), the accelerometer 102 determines the pulse wave based on an acceleration signal incurred by the pulse wave at the measuring point, as is described in the arrangement 200 in FIG. 2.

The arrangement 200, or advantageously the wristband device 201 comprises means, such as the data processing device 107, 111 to determine the first trigger signal at the moment of said cardiac systole ejection (when receiving measuring signal from the measuring device, such as from the accelerometer), and a second trigger signal at the moment of said pulse wave, which both can be determined by the same accelerometer 102 according to an advantageous embodiment. Then these measuring devises can be integrated into the same device, such as to a wristband device 201, for example.

According to an embodiment, as described in FIGS. 1 and 2, the arrangement 100, 200 may also comprise a separate accelerometer 102, which is configured to be placed near the heart and to determine a cardiac systole based on an acceleration signal there. The arrangement may also comprise a vibration device 108 at the wristband device 101, 201 for generating a vibrational signal to the body of the user. The accelerometer 102 is then advantageously configured to determine an acceleration signal incurred by the vibration device for determining the distance between the heart and the measuring point as is described in this document.

The data processing device 107, 111 for determining the PTT, PWV and/or blood pressure or the like may be comprised at the (external) backend system 110, such as at a server, laptop, tablet computer, mobile phone or cloud base system, whereupon the arrangement 100, 200 is configured to transfer 105 the measured trigger signals (or measured raw data) to said data processing unit, and where said data processing unit is configured to determine the trigger signals, pulse transit time, pulse wave velocity and/or arterial blood pressure; and/or the distance. However, also the wristband device 101, 201 may comprise said data processing device for that purpose.

FIGS. 3 and 4 illustrate exemplary devices 101, 201 for determining pulse transit time according to an advantageous embodiment of the invention. Both the device comprises advantageously an accelerometer 102 and a pulse wave sensor 102, 103 for sensing a pulse wave. According to an embodiment 100 described in FIG. 3 the accelerometer may be as a separate accelerometer 102 to be placed essentially at the point of the heart, whereupon the accelerometer is advantageously configured to communicate with the wristband device 101. According to an embodiment 200 described in FIG. 4 the accelerometer 102 may be integrated to the wristband device 201.

According to an embodiment the device 101, 201 may comprise also the data processing device 107 for processing data, and/or a data communication device 104 for communicating the first and second trigger signals to an outer data processing device (backend) 110 for determination and calculations.

The device is advantageously a wristband device comprising the pulse wave sensor 103 integrated into said wristband device and the accelerometer 102. The accelerometer 102 may be as a separate module (arrangement 100 and device 101) and being in data communication with the device 101 as such, or the device 201 may comprise both the pulse wave sensor 103 and the accelerometer 101 (arrangement 200 and device 201).

According to an embodiment the device 101, 201 may also comprise a vibrator 108 for producing vibrational signal.

The invention has been explained above with reference to the aforementioned embodiments, and several advantages of the invention have been demonstrated. It is clear that the invention is not only restricted to these embodiments, but comprises all possible embodiments within the spirit and scope of the inventive thought and the following patent claims.

The invention claimed is:

1. A wristband device comprising:
an accelerometer configured to determine a cardiac systole based on an acceleration signal induced by a heart at the moment of the cardiac systole, wherein the accelerometer is further configured to be used as a pulse wave detecting device and detect a pulse wave, at a measuring point, based on an acceleration signal induced by the pulse wave at the measuring point, and
a data processing device configured to determine a first trigger signal at the moment of said cardiac systole, and a second trigger signal at the moment when said pulse wave is detected at the measuring point, and
wherein the data processing device is further configured to determine a pulse transit time as a time difference between said first and second trigger signals,
wherein a separate accelerometer near the heart is configured to determine an acceleration signal incurred by a vibration of a vibration device positioned at the measuring point, and
wherein the data processing device is further configured to determine a distance between the heart and the measuring point based on a time difference between the moment of vibration and the moment that the vibration is detected by the separate accelerometer.

2. The wristband device of claim 1, wherein the data processing device is further configured to determine a pulse wave velocity based on said time difference and a distance between the heart and the accelerometer, and determine an arterial blood pressure from the pulse wave velocity.

3. The wristband device of claim 1, wherein the data processing device is configured to use a speed of sound as a speed of the acceleration signal induced by the heart at the moment of the cardiac systole.

4. The wristband device of claim 1, wherein the wristband device is configured to send the first and second trigger signals, or data measured by the accelerometer from which the first and second trigger signals may be derived, to a backend system, and wherein said backend system is configured to determine the pulse transit time, a pulse wave velocity and/or an arterial blood pressure.

5. The wristband device of claim 1, wherein the wristband device further comprises at least one of a gyroscope or a magnetometer.

6. A method comprising:
providing, on a wrist of a user, a wristband device comprising an accelerometer;
determining, with the accelerometer of the wristband device, a cardiac systole based on an acceleration signal induced by a heart at the moment of the cardiac systole,
determining, by the accelerometer, a pulse wave, at a measuring point, based on an acceleration signal due to the pulse wave at the measuring point,
determining, by a data processing device, a first trigger signal at the moment of said cardiac systole, and a second trigger signal at the moment when said pulse wave is determined at the measuring point,
determining, by the data processing device, a pulse transit time as a time difference between said first and second trigger signals,
causing, by a vibration device positioned at the measuring point, a vibration to incur an acceleration signal for detection by a separate accelerometer near the heart, and
determining, by the data processing device, a distance between the heart and the measuring point based on a time difference between the moment of vibration and the moment that the vibration is detected by the separate accelerometer.

7. A computer program product for determining pulse transit time, comprising program code stored on a non-transitory computer-readable medium, which program code is configured, when executed by a processor, to cause the wristband device of claim 1 to perform:
determining, with the accelerometer of the wristband device, a cardiac systole based on an acceleration signal induced by a heart at the moment of the cardiac systole,
determining, by the accelerometer, a pulse wave, at a measuring point, based on an acceleration signal due to the pulse wave at the measuring point,
determining, by a data processing device, a first trigger signal at the moment of said cardiac systole, and a second trigger signal at the moment when said pulse wave is determined at the measuring point,
determining, by the data processing device, a pulse transit time as a time difference between said first and second trigger signals,
causing, by a vibration device positioned at the measuring point, a vibration to incur an acceleration signal for detection by a separate accelerometer near the heart, and
determining, by the data processing device, a distance between the heart and the measuring point based on a time difference between the moment of vibration and the moment that the vibration is detected by the separate accelerometer.

8. The wristband device of claim 4, wherein the wristband device further comprises a wireless data device configured to communicate the measurement signals to the backend system.

9. The wristband device of claim 8, wherein the backend system is one of: a server, a laptop, a tablet computer, a mobile phone or a cloud based system.

10. The method of claim 6, wherein a pulse wave velocity is determined based on said time difference and a distance between the heart and the accelerometer, and an arterial blood pressure is determined from the determined pulse wave velocity.

11. The method of claim 6, further comprising sending the first and second trigger signals to a backend system, and wherein said backend system is configured to determine the pulse transit time, pulse wave velocity and/or arterial blood pressure.

12. A system comprising:
a wristband device comprising an accelerometer configured to determine a cardiac systole based on an acceleration signal induced by a heart at the moment of the cardiac systole, wherein the accelerometer is further configured to be used as a pulse wave detecting device and detects a pulse wave, at a measuring point, based on an acceleration signal induced by the pulse wave at the measuring point,
a data processing device configured to determine a first trigger signal at the moment of said cardiac systole, and a second trigger signal at the moment when said pulse wave is detected at the measuring point, and
a backend system configured to determine a pulse transit time, a pulse wave velocity and/or an arterial blood pressure,
wherein the wristband device comprises a data communication device configured to communicate (i) the acceleration signals measured by the accelerometer or (ii) the first trigger signal and the second trigger signal to the backend system; and
wherein the system further comprises a vibration device to be positioned at the measuring point, whereupon a separate accelerometer near the heart is configured to determine an acceleration signal incurred by a vibration of the vibration device and the system is configured to determine a distance between the heart and the measuring point based on a time difference between the moment of vibration and the moment that the vibration is detected by the separate accelerometer.

13. The system of claim 12, wherein the data processing device is comprised in the backend system.

14. The system of claim 12, wherein the backend system is one of: a server, a laptop, a tablet computer, a mobile phone or a cloud based system.

* * * * *